US010441916B2

(12) United States Patent
Chen

(10) Patent No.: US 10,441,916 B2
(45) Date of Patent: Oct. 15, 2019

(54) AIR PURIFIER

(71) Applicant: GUANGZHOU MERCI FOREST ENVIRONMENT SCIENCE AND TECHNOLOGY CO., LTD., Guangzhou (CN)

(72) Inventor: Zhuoquan Chen, Guangzhou (CN)

(73) Assignee: GUANGZHOU MERCI FOREST ENVIRONMENT SCIENCE AND TECHNOLOGY CO., LTD., Guangzhou (CN)

(*) Notice: Subject to any disclaimer, the term of this patent is extended or adjusted under 35 U.S.C. 154(b) by 158 days.

(21) Appl. No.: 15/744,070

(22) PCT Filed: Jun. 28, 2016

(86) PCT No.: PCT/CN2016/087446
§ 371 (c)(1),
(2) Date: Jan. 12, 2018

(87) PCT Pub. No.: WO2017/008628
PCT Pub. Date: Jan. 19, 2017

(65) Prior Publication Data
US 2018/0200665 A1 Jul. 19, 2018

(30) Foreign Application Priority Data
Jul. 14, 2015 (CN) .......................... 2015 1 0410752

(51) Int. Cl.
*F24F 1/00* (2019.01)
*B01D 53/14* (2006.01)
(Continued)

(52) U.S. Cl.
CPC ........... *B01D 53/1425* (2013.01); *A01G 9/02* (2013.01); *A01G 27/005* (2013.01); *A61L 9/20* (2013.01);
(Continued)

(58) Field of Classification Search
CPC ........... A01G 27/005; A01G 9/02; A61L 9/20; A61L 2209/14; C02F 3/32; C02F 3/348;
(Continued)

(56) References Cited

U.S. PATENT DOCUMENTS 5,277,877 A * 1/1994 Jeffrey .................... A61L 9/122
47/66.6
5,397,382 A * 3/1995 Anderson ................ A01G 9/02
96/135
(Continued)

FOREIGN PATENT DOCUMENTS

CN 202860312 A 4/2013
CN 103157373 A 6/2013
(Continued)

OTHER PUBLICATIONS

International Search Report dated Sep. 13, 206 in PCT application PCT/CN2016/087446.
(Continued)

*Primary Examiner* — Frank M Lawrence, Jr.
(74) *Attorney, Agent, or Firm* — Kilpatrick Townsend & Stockton LLP

(57) ABSTRACT

Disclosed is an air purifier, which comprises a shell with an air inlet and an air outlet, an ecological purification system with a flowerpot assembly, a microorganism box and a water tank arranged in sequence, a filtering system, and a control system for carrying out control. The water of the ecological purification system flows through the filtering system to bring dust and VOCs adsorbed by the filtering system into the ecological purification system for purification. The flowerpot assembly comprises a flowerpot. The water of the water tank enters the flowerpot via a water inlet, and when the water level is higher than a water outlet, the water flows through the microorganism box and then enters the water tank, so as to form the water circulation. The air purifier is (Continued)

simple in structure, easy to operate and low in cost, and has a high purification efficiency for air pollutants, especially VOCs.

15 Claims, 2 Drawing Sheets

(51) Int. Cl.
 A01G 9/02 (2018.01)
 A01G 27/00 (2006.01)
 A61L 9/20 (2006.01)
 B01D 46/00 (2006.01)
 B01D 46/10 (2006.01)
 B01D 47/02 (2006.01)
 B01D 50/00 (2006.01)
 C02F 3/32 (2006.01)
 C02F 3/34 (2006.01)
 C12M 1/12 (2006.01)
 F24F 3/16 (2006.01)
 B01D 53/18 (2006.01)
 C02F 103/18 (2006.01)

(52) U.S. Cl.
 CPC ..... *B01D 46/0023* (2013.01); *B01D 46/0036* (2013.01); *B01D 46/10* (2013.01); *B01D 47/022* (2013.01); *B01D 50/006* (2013.01); *B01D 53/1412* (2013.01); *B01D 53/1487* (2013.01); *C02F 3/32* (2013.01); *C02F 3/348* (2013.01); *C12M 37/02* (2013.01); *F24F 3/1603* (2013.01); *A61L 2209/111* (2013.01); *A61L 2209/134* (2013.01); *A61L 2209/14* (2013.01); *B01D 53/1493* (2013.01); *B01D 53/185* (2013.01); *B01D 2252/103* (2013.01); *B01D 2257/708* (2013.01); *B01D 2258/06* (2013.01); *B01D 2259/804* (2013.01); *C02F 2103/18* (2013.01); *F24F 2003/1653* (2013.01); *F24F 2003/1671* (2013.01); *Y02A 50/235* (2018.01)

(58) Field of Classification Search
 CPC ............ C02F 2103/18; B01D 46/0023; B01D 46/0036; B01D 46/10; B01D 47/022; B01D 50/006; B01D 53/1412; B01D 53/1425; B01D 53/1487; B01D 53/1493; B01D 53/185; B01D 2252/103; B01D 2257/708; B01D 2258/06; B01D 2259/804; C12M 37/02; Y02A 50/235; F24F 3/1603; F24F 2003/1653; F24F 2003/1671
 USPC ..................... 96/224, 243, 322, 371; 55/315
 See application file for complete search history.

(56) References Cited

U.S. PATENT DOCUMENTS

| 5,407,470 | A | * | 4/1995 | Jutzi | ........................ | A01G 9/00 |
| | | | | | | 96/121 |
| 2002/0104436 | A1 | * | 8/2002 | Logstrup | ................ | B01D 53/85 |
| | | | | | | 95/90 |
| 2011/0154985 | A1 | * | 6/2011 | Mittelmark | ............ | A01G 27/00 |
| | | | | | | 95/1 |
| 2014/0190078 | A1 | | 7/2014 | Kim et al. | | |

FOREIGN PATENT DOCUMENTS

| CN | 203533726 U | 4/2014 |
| CN | 104221833 A | 12/2014 |
| CN | 104296258 A | 1/2015 |
| CN | 104307356 A | 1/2015 |
| CN | 204191225 U | 3/2015 |
| CN | 104964348 A | 10/2015 |
| CN | 204880365 U | 12/2015 |

OTHER PUBLICATIONS

First Official Action of issued in the priority Chinese application CN201510410752.X and search report.

\* cited by examiner

AIR PURIFIER

CROSS-REFERENCE TO RELATED APPLICATIONS

This application is a National Stage of International Application No. PCT/CN2016/087446, filed on Jun. 28, 2016, which claims priority to and benefits of Chinese Patent Applications Serial No. 201510410752.X, filed with the State Intellectual Property Office of P. R. China on Jul. 14, 2015, the entire contents of which are incorporated herein by reference.

TECHNICAL FIELD

The present disclosure relates to the field of air purification, in particular to an air purifier.

BACKGROUND OF THE INVENTION

High-speed urbanization causes that indoor and outdoor air is all to a certain extent polluted by dusts and toxic gas, combined with building materials, furniture and electrical equipments, etc. continue to release large amounts of VOCs (toxic and harmful volatile organic compounds) indoors, making the indoor air quality becomes worrying, and affects people's healthy and comfortable lives directly.

At present, the purification methods of air purifiers on the market mainly include chemical reaction methods, physical adsorption technology, ozone anion technology, nano-photocatalys is technology, low temperature plasma technology, plant purification and biodegradation, etc. Most air purifiers are all required to replace internal arrangements regularly, which results in expensive maintenances thereof. Most mechanical purifiers can only filter out dusts in air, but can not remove VOCs effectively. In general, plant air purifiers use the roots, stems and leaves of the plant to absorb the VOCs in the air to purify the air, such as the plant air purifier and the system thereof disclosed in Chinese Patent No. ZL201310214831.4. In such kind of plant air purifiers, plant body is the core system of air purification, and the plant's own air purification effect is limited and not targeted, if there are not any other means of auxiliary air purification to employ, the purification effect of plant air purifiers will difficult to achieve the desired level. Microbiological purification of air is mainly use the assimilation of microbial populations, which are of wide distribution, vigorous metabolism and rapid propagation, to degrade the VOCs in air, so as to achieve the purpose of purifying air, such as the air purifier for removing formaldehyde as disclosed in the Chinese Patent Application No. 201410607342.X. However, it is required to replenish with microorganisms often because they are dead-prone, and the usage is cumbersome and costly expensive.

Chinese Patent No. ZL201420592198.2 discloses an indoor air purifier which is provided with a biological purification layer and a plant planting position. The air purifier enables a symbiosis of plant roots and microorganisms in water by means of extending the plant roots under water, and meantime takes advantage of the purification effect of plants and microorganisms to build a complete ecosystem so as to secure the growth of plants, the long-term survival of microorganisms and to remove dusts and VOCs effectively. Nevertheless in this technology only when the plant roots extend under the water surface in the water tank, then the symbiosis of the plants and the microorganisms can be secured. This configuration has a certain limitation to the water level where the water level should not be too much low. Because the plant roots are positioned in the water tank, mud adsorbed on the roots, broken or falling roots may also be in the water tank, which may affect the water circulation and the purification effect.

BRIEF SUMMARY OF THE INVENTION

One object of the present disclosure is to provide an air purifier that has simple and compact structure, simple operation, is capable of removing indoor dusts and VOCs effectively, and is of high purification efficiency and environment friendly.

The present disclosure is achieved by the following solutions:

An air purifier, comprising a shell provided with an air inlet and an air outlet; and further including a control system, and an ecological purification system and a filtering system which are connected to the control system; water in the ecological purification system flowing through the filtering system, to bring dusts and VOCs adsorbed by the filtering system into the ecological purification system for purification, wherein the ecological purification system includes a flowerpot assembly capable of planting plants, a microorganism box capable of accommodating microorganisms and a water tank capable of holding water, arranged in sequence; wherein the flowerpot assembly includes a flowerpot provided with a water inlet and a water outlet; and the ecological purification system is provided with a following water circulation: water in the water tank enters the flowerpot via the water inlet of the flowerpot, and when a water level in the flowerpot is higher than the water outlet of the flowerpot, the water flows through the microorganism box via the water outlet of the flowerpot, and then enters the water tank.

A further modified solution of the present disclosure includes that:

The filtering system includes a filtering layer including a primary filtering layer, a secondary filtering layer capable of adsorbing dusts and a water curtain capable of adsorbing VOCs and dusts, which are arranged in sequence between the air inlet and the air outlet; both ends of the water curtain being respectively in fluid communication with the water outlet of the flowerpot and the microorganism box.

The ecological purification system further includes a water diverter assembly provided between the flowerpot and the water curtain, wherein the water diverter assembly is provided with at least one water outlet and at least one water inlet; the water inlet of the water diverter assembly is in fluid communication with the water outlet of the flowerpot, and the water outlet of the water diverter assembly is in fluid communication with the water curtain.

The microorganism box is provided therein with fillers which are capable of adsorbing dusts, VOCs and microorganisms.

A drainage outlet is provided at the bottom of the water tank, the drainage outlet being detachably connected with a closing element matching therewith.

The water curtain is adopted a water absorbent material and/or an antibacterial material, and preferably formed by folding a water absorbent material and/or an antibacterial material.

The ecological purification system further includes a water pump connected to the control system, and a drawing pipe assembly connected with the water pump, and configured to introduce the water from the water tank to the water inlet of the flowerpot.

The flowerpot is further provided with an overflow hole positioned higher than the water outlet of the flowerpot; the ecological purification system further includes a return pipe assembly connected to the overflow hole of the flowerpot so as to introduce excessive water into the water tank when the water level in the flowerpot is higher than the overflow hole.

The air purifier further includes a monitor connected to the control system and configured to monitor air quality.

The control system includes a circuit board, a function key and a display.

The water outlet of the flowerpot is provided with a first filter screen capable of preventing the water outlet of the flowerpot from being blocked by plant roots.

The control system includes a toppling switch capable of automatically cutting off the power when the air purifier is toppling.

The filtering system further includes a fan device connected with the control system, and the fan device includes a wind rotor, an electric motor capable of driving the wind rotor and a wind guide tube guiding the wind caused by the rotating of the wind rotor to the air outlet.

The air purifier further includes an ultraviolet lamp assembly provided between the wind rotor and the air outlet.

The flowerpot assembly further includes a flowerpot support configured to support the flowerpot, a flowerpot sealing ring configured to seal the flowerpot and the flowerpot support, and a flowerpot cover configured to close the flowerpot.

The water tank is provided with a water-tank separator configured to seal the water tank and further to prevent the water in the water tank from overflowing when the air purifier is toppling, and the water-tank separator is provided inside or on the top of the water tank, and hermetically connected with the water tank.

The air purifier is further provided with a water adding inlet capable of adding water from outside, the water adding inlet being provided with a second filter screen; the water adding inlet is in direct communication with the water tank through a water pipe assembly, or the water adding inlet is provided on the flowerpot, so that the water adding inlet is in fluid communication with the water tank by the communication between the water adding inlet and the flowerpot.

The water tank is provided with a water level sensor connected with the control system.

The flowerpot is of cone shape; the flowerpot is positioned above the air outlet, and purified air exhausted from the air outlet is blown upwards to the bottom and/or the outer surface of the flowerpot, leaving the purified air blocked to change the wind direction to form a turbulent flow.

An air outlet cover is provided on the air outlet; the air outlet cover is provided with a plurality of vents distributed in dots, and the purified air exhausted from the vents is blown to the bottom and/or the outer surface of the flowerpot. Due to the different positions of the vents, the wind directions after being blocked are different as well. The airflows in all directions thus form a turbulent flow to accelerate the indoor air flow.

The microorganisms include at least one microorganism that is capable of degrading VOCs.

The microorganism includes one or more selected from the group consisting of *Pseudomonas, Bacillus, Streptomyces, Mucor, Aspergillus, Penicillium, Rhizopus* and *Alternaria*.

The microorganism is a combination of the *Pseudomonas* and other microorganism populations. The other microorganism populations may be selected from the group consisting of *Bacillus, Streptomyces, Mucor, Aspergillus, Penicillium, Rhizopus, Alternaria* and the like.

The data sensed by the sensor assembly of dusts and/or VOCs may be displayed on the display. The sensor assembly of dusts and/or VOCs may also be connected to a warning device which shall alarm when the monitored data exceeds a predetermined threshold value.

The beneficial effects of the present disclosure are that: the air purifier of the present disclosure is of simple and compact structure, simple operation. The sequential arrangement of the flowerpot assembly, the microorganism box and the water tank, is capable of effectively avoiding the massive presence of the plant roots in the water tank which causes the problem that the water circulation becomes not smooth, and of smooth water circulation. On one hand the symbiosis of microorganisms and plant roots establishes a complete ecosystem, which is beneficial to the healthy growth of plants and the long-term survival of microorganisms; on the other hand, microorganisms and plants are used together to efficiently remove dusts and VOCs. That is, the air is mainly purified by the ecological purification system consisted of plants and microorganisms, which can efficiently remove dusts and VOCs. The air purifier is of high purification efficiency and environment friendly. When being applied indoors, planting plants is not only capable of increasing the oxygen content of indoor air, of absorbing VOCs and of purifying dusts, but also of removing the indoor dusts and VOCs effectively by the degrading ability of the microorganisms against VOCs. It may have the possibility to purify air, while planting the plants, which saves resources.

Wherein: 1—shell, 101—air inlet, 102—air outlet, 2—control system, 201—circuit board, 202—function key, 203—display, 301—flowerpot assembly, 3011—flowerpot, 30111—water outlet of the flowerpot, 3012—flowerpot support, 3013—flowerpot sealing ring, 3014—flowerpot cover, 302—microorganism box, 303—water tank, 3031—closing element, 304—water diverter assembly, 306—drawing pipe assembly, 4—filtering system, 401—filtering layer, 4011—primary filtering layer, 4012—secondary filtering layer, 4013—water curtain, 402—fan device, 4021—wind rotor, 4022—electric motor, 4023—wind guide tube, 5—ultraviolet lamp assembly.

DETAILED DESCRIPTION OF THE INVENTION

The air purifier of the present disclosure will be further described below with reference to the accompanying figures.

Example 1

Figure 1:
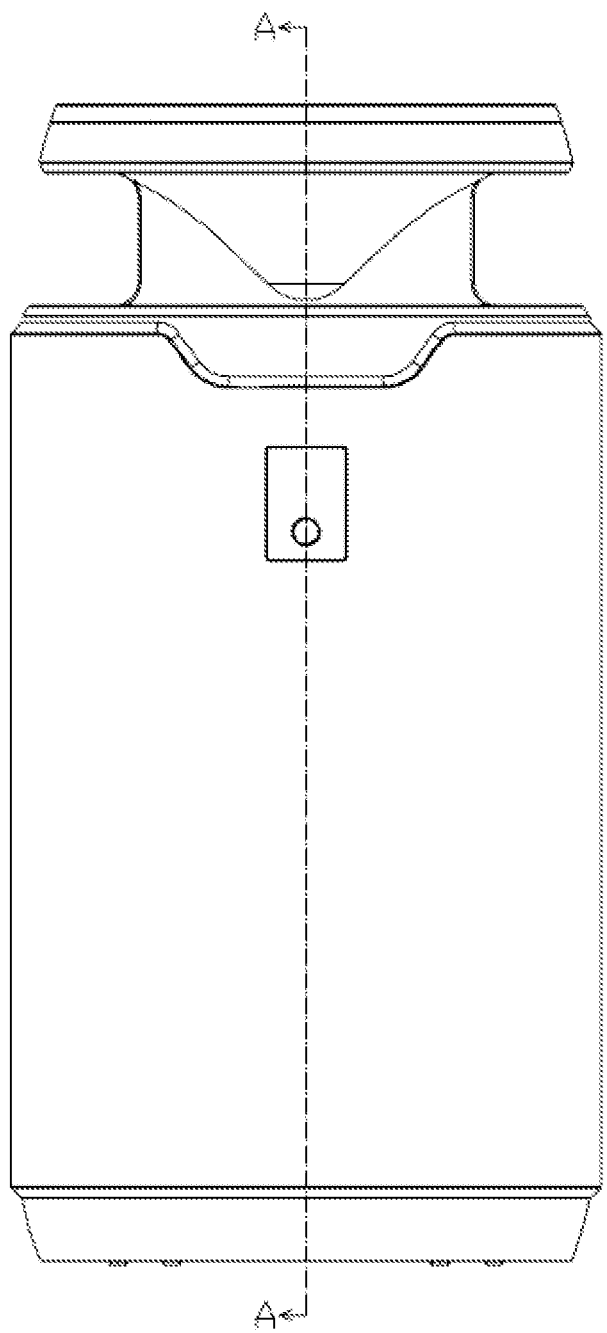
FIG. 1 shows a schematic structural view of the air purifier of the present disclosure.
Figure 2:
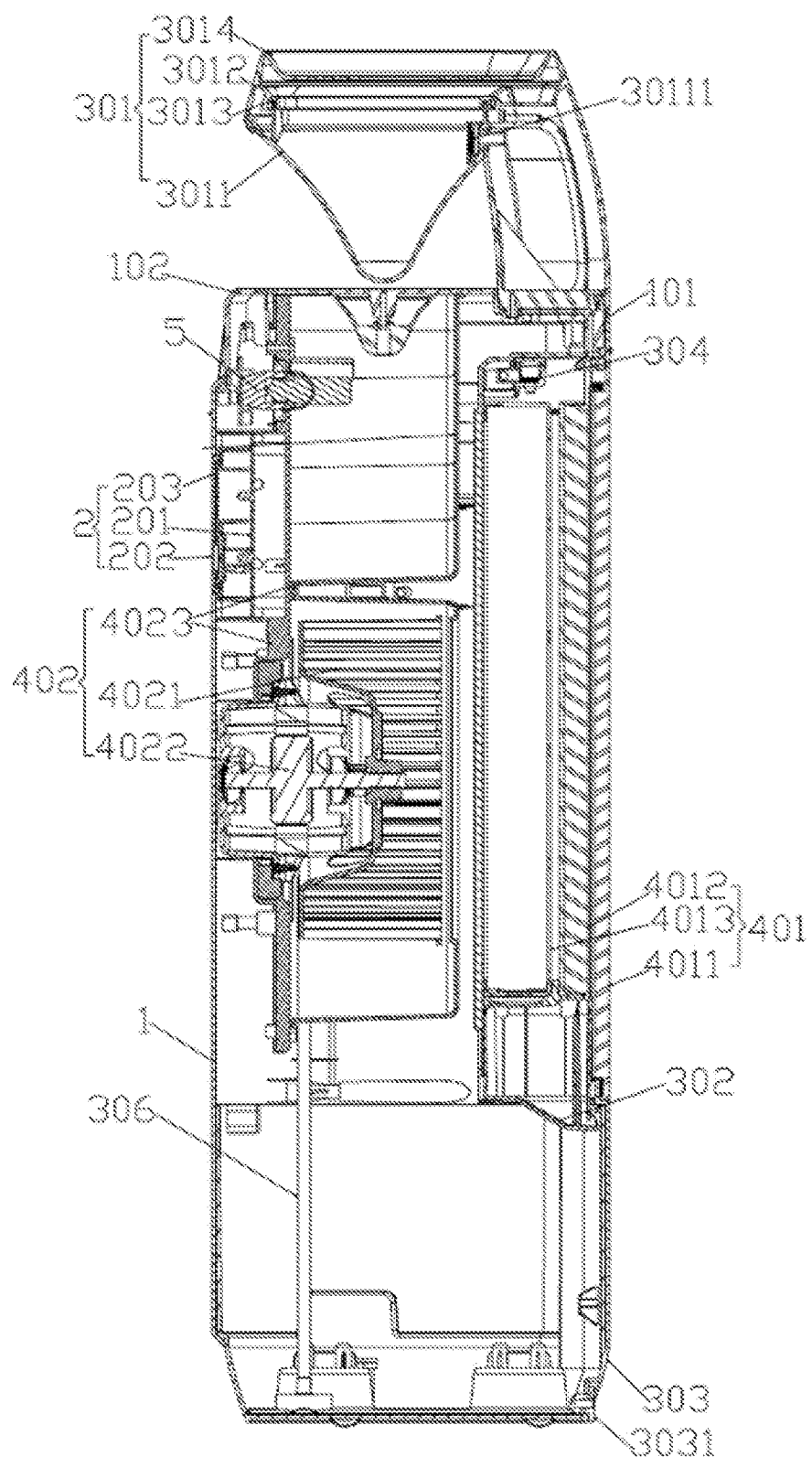
FIG. 2 shows a cross-sectional view along the line A-A in FIG. 1.

As shown in FIG. 1 and FIG. 2, an air purifier of the present disclosure includes a shell 1, a control system 2 and an ecological purification system and a filtering system 4 which are connected to the control system 2. The shell 1 is provided with an air inlet 101 and an air outlet 102. Water in the ecological purification system passes through the filtering system 4, and brings dusts and VOCs adsorbed by the filtering system 4 into the ecological purification system for purification. The ecological purification system includes a flowerpot assembly 301 capable of planting plants, a microorganism box 302 capable of accommodating microorganisms and a water tank 303 capable of holding water, arranged in sequence; wherein the flowerpot assembly 301 includes a flowerpot 3011 provided with a water inlet and a water outlet; and the ecological purification system is provided with a following water circulation: water in the water tank 303 enters the flowerpot 3011 via the water inlet of the flowerpot 3011, and when a water level in the flowerpot 3011 is higher than the water outlet 30111 of the flowerpot, the water flows through the microorganism box via the water outlet 30111 of the flowerpot, and then enters the water tank 303.

The structure of the air purifier is simple and compact. The sequential arrangement of the flowerpot assembly 310, the microorganism box 302 and the water tank 303, is capable of effectively avoiding the massive presence of the plant roots in the water tank which lead to a blockage of water circulation channel, to ensure that the dusts, the VOCs and the microorganisms can enter the water circulation successfully. With the driving of the water circulation, the microorganisms can enter the flowerpot to have a symbiosis with the plant roots. The dusts can enter the flowerpot to be absorbed by the plant roots. The microorganisms can degrade the VOCs through the entire water circulation process and can remove dusts and VOCs effectively and has a high purification efficiency. The water inlet and outlet are provided on the flowerpot, thus it can ensure that the water inside the air purifier forms an internal circulation without adding any other structures additionally. The air purifier is simple to use and operate. It can replenish the water circulation with the required water and microorganisms by means of watering the flowerpot directly, or replenish the water tank with water or the microorganism box with microorganisms in other manners. The air purifier purifies the air via the internal circulation of water inside the air purifier through the ecosystem, and it is environment friendly.

A separate water tank 303 may be provided or not provided. The flowerpot 3011 serves not only as a flowerpot to plant plants, but also as a water tank for holding water.

When in use, the microorganisms in the microorganism box 302 can flow through the flowerpot to have a symbiosis with the plants planted in the flowerpot, with the driving of the water circulation. Air enters via the air inlet 101 provided on the shell 1, dusts and VOCs are adsorbed on the filtering system 4 when the air passes through the filtering system 4. Under the effect of the water circulation, dusts and VOCs enter into the ecological purification system, wherein the microorganisms purify the VOCs and the plant roots adsorb the dusts. Certainly the plants can also absorb a part of the VOCs. The purified air is exhausted out of the air purifier via the air outlet 102.

Preferably, the filtering system 4 includes a filtering layer 401 including a primary filtering layer 4011, a secondary filtering layer 4012 capable of adsorbing dusts and a water curtain 4013 capable of adsorbing VOCs and dusts, which are arranged in sequence between the air inlet 101 and the air outlet 102. Both ends of the water curtain 4013 are respectively in fluid communication with the water outlet 30111 of the flowerpot and the microorganism box 302. The primary filtering layer 4011 is capable of preventing large impurities such as animal hairs from entering the air purifier so as to prevent the blocking of the air purifier. The secondary filtering layer 4012 is capable of preventing large particle contaminants such as dusts, pollens and etc. from entering the air purifier. The water curtain 4013 is capable of adsorbing dusts with smaller sizes (e.g. PM2.5) and VOCs. Under the effects of the three filtering layers, it not only ensures that the dusts and VOCs in air can enter the air purifier successfully for purification, but also reduces the cleaning intensity to prevent the airflow channels and the water circulation channels of the air purifier from being blocked. The water curtain can direct the dusts and VOCs absorbed thereon into the microorganism box 302 through the water outlet 30111 of the flowerpot. Preferably, the flowerpot assembly 301 is positioned above the water curtain 4013, and the microorganism box 302 is positioned under the water curtain 4013. On the one hand this construction makes the structure more compact, and on the other hand since the flowerpot 3011 of the flowerpot assembly 301 is positioned above, when the water level in the sub-pot is higher than the water outlet 30111 of the flowerpot, then the water flows out naturally and under the gravity effect, the dusts and VOCs thereon is taken away through the water curtain 4013, which avoid an excessive rapid water flow which may be splashed on the filtering layer 401 and may cause the entering of the microorganisms into the room at the position of the filtering layer 401.

Preferably, the water curtain 4013 employs the water absorbent material and/or the antibacterial material, such as the water curtain 4013 employs the water absorbent antibacterial microporous material. The water absorbent material is easily to adsorb dusts and VOCs. The antibacterial material is not easily to adsorb the microorganisms, so that the microorganisms can cycle quickly, and can have a symbiosis with the plants in water, which increases the microbial survival time. Preferably, the water curtain is formed by folding the water absorbent material and/or the antibacterial material, which increases the surface area, so as to enlarge the contacting area with air, which is more advantageous to adsorb dusts and VOCs and improves the purification efficiency.

Preferably, the ecological purification system further includes a water diverter assembly 304 provided between the flowerpot 3011 and the water curtain 4013. The water diverter assembly 304 is provided with at least one water outlet and at least one water inlet. The water inlet of the water diverter assembly 304 is in fluid communication with the water outlet of the flowerpot 30111, and the water outlet of the water diverter assembly is in fluid communication with the water curtain 4013. This configuration of the water diverter assembly 304 can direct the water circulation paths to enable the water to flow out from the flowerpot and to pass through the water curtain uniformly, bringing dusts and VOCs adsorbed on the water curtain into the microorganism box 302.

Preferably, the microorganism box 302 is provided therein with fillers which are capable of adsorbing dusts, VOCs and microorganisms. When in use, it is only required to add microorganisms. The added microorganisms include at least one microorganism capable of degrading VOCs, such as the microorganism is a combination of *Pseudomonas* and other microorganism populations. The other microorganism populations may be selected from the group consisting of *Bacillus, Streptomyces, Mucor, Aspergillus, Penicillium, Rhizopus, Alternaria* and the like. The addition of the fillers is beneficial for the absorption of microorganisms, dusts and VOCs. In such a context, the microorganisms are capable of degrading more dusts and VOCs. The microorganisms in the microorganism box 302 may also be fixed in the fillers so as to keep a certain number of the microorganisms in the microorganism box 302. The purification process occurs mainly in the microorganism box 302. In addition a small part of the escaping microorganisms will cycle with the water circulation, and purify air in the water curtain, water tank and flowerpot. The fixing of the microorganisms may use the entrapment method to form a microporous gel with sodium alginate and calcium chloride. The contaminants enter into the inside of the gel through the micropores to be purified by the microorganisms.

Preferably, a drainage outlet is provided at the bottom of the water tank 303, and the drainage outlet is detachably connected with a closing element 3031 matching therewith, so as to exhaust the water in the water tank 303 conveniently when necessary.

Preferably, the water tank 303 is provided with a water-tank separator configured to seal the water tank 303 and further to prevent the water in the water tank 303 from overflowing when the air purifier is toppling, and the water-tank separator is provided inside or on the top of the water tank 303, and hermetically connected with the water tank 303. This configuration is capable of preventing the water from splashing on electrical devices such as controller and fan during the process of water adding or water circulation, which prevents corrosion of the internal configuration, and is also capable of preventing the water in the water tank 303 from overflowing when the air purifier is toppling so as to protect the internal configuration of the air purifier and to ensure the use safety.

Preferably, the ecological purification system further includes a water pump connected to the control system 2, and a drawing pipe assembly 306 connected to the water pump, and configured to introduce the water from the water tank 303 to the water inlet of the flowerpot 3011. In such a configuration, under the effect of the water pump, the water in the water tank 303 can enter the flowerpot assembly 301 via the drawing pipe assembly 306. The water returns to the water tank through the flowerpot assembly 301 and then through the microorganism box 302. In such a way an internal water circulation is formed in the air purifier, which can save water, and the microorganisms in the microorganism box 302 may flows through the water circulation. The air purification process may proceed in the flowerpot assembly 301, the microorganism box 302, the water tank 303 and the water curtain 4013 (if there is provided with a structure of the water curtain 4013). The purification process is that: the water curtain 4013 intercepts dusts and VOCs in air; under the effect of the water, the dusts and VOCs enter into the microorganism box 302, where the dusts are adsorbed onto the biological purification layer 301, the VOCs are purified in the microorganism box 302, and the dusts enter the flowerpot assembly 301 through the water circulation to be absorbed by the plant roots for using. In addition during the process of the water circulation, the microorganisms in the flowerpot assembly 301, the water curtain 4013 and the water tank 303 can respectively purify a part of VOCs.

Preferably the filtering system 4 further includes a fan device 402 connected with the control system 2, and the fan device 402 includes a wind rotor 4021, an electric motor 4022 capable of driving the wind rotor 4021 and a wind guide tube 4023 guiding the wind caused by the rotating of the wind rotor to the air outlet 102, which can accelerate the air flow and improve the purification efficiency. The water curtain 4013 has a folding design, through which the airflows should pass in a bending manner, so that the contacting and exchanging area of the polluted air and the water is greatly increased. Meantime, due to the effect of the fan device, the pressure is suddenly reduced after the air has passed through the water curtain, thus a pressure difference between the front and the rear of the water curtain is formed, such that the water molecules evaporate rapidly in the folded layers of the water curtain to form air mist masses. Contaminants are wrapped in the air mist masses, and are brought by the water flow into the microorganism box 302 when the water flow from the water diverter flows through the water curtain, where the organic contaminants such as formaldehyde, benzene and the like are degraded by the microorganisms into carbon dioxides and water. The carbon dioxides into the air can be adsorbed by plant leaves for photosynthesis to be transferred into oxygen, while nitrate, sulfate, ammonium salt and sodium salt etc. in dusts/particles (PM 2.5) enter the flowerpot through the water circulation system, and then are absorbed by plant roots for use.

Preferably, the air purifier further includes an ultraviolet lamp assembly 5 provided between the wind rotor 4021 and the air outlet 102, which is capable of creating ultraviolet for sterilization. Preferably, the ultraviolet lamp is arranged opposite to the air inlet of the wind rotor, wherein the wind rotor 4021 may be a turbine exhaust fan. The air inlet of the turbine fan is relatively small, such that on the one hand the effects of the ultraviolet may be concentrated, and it does not need too large area of radiation, and on the other hand, it does not need too much power. Meanwhile, in order to prevent the generation of ozone, it is preferably to use an ultraviolet lamp that emits only the light with 254 nm wavelength. In order to prevent the ultraviolet leakage, there is provided a protective cover outside the lamp tube, so that it will not cause harm to the human body. The ultraviolet lamp assembly 5 performs a sterilization operation to provide a further purification guarantee, which may kill the microorganisms permeating through the water curtain 4013 or via the pores on the edges thereof, to prevent the microorganisms from causing a secondary pollution to air.

Preferably, the flowerpot 3011 is further provided with an overflow hole positioned higher than the water outlet 30111 of the flowerpot; and the ecological purification system further includes a return pipe assembly connected to the overflow hole of the flowerpot 3011 so as to introduce excessive water into the water tank 303 when the water level in the flowerpot 3011 is higher than the overflow hole. When the water is too much during the process of directly adding water to the flowerpot 3011, the water may directly flow into the water tank via the overflow hole through the return pipe assembly, to prevent the water from diffusing from the flowerpot 3011 into the room due to the excessive water.

Preferably, the control system 2 includes a circuit board 201, a function key 202 and a display 203, wherein the function key 202 may be provided on the shell 1. When in use, it is only required to operate the function key 202, then it is capable of adjusting the respective functions (such as wind speed etc.), wherein the display 203 may be configured to display the respective function parameters of the air purifier.

Preferably, the air purifier further includes a monitor connected to the control system 2 and configured to monitor the air quality. The monitor may include dusts and/or VOCs sensor assembly. Preferably, the monitor configured to monitor the air quality is provided on the shell 1, and is connected to the display 203 of the control system. The display 203 can display if the contents of dusts and formaldehyde in the air have exceeded the standard. Users can know the air quality, in order to take relevant protection measures.

Preferably, the water outlet 30111 of the flowerpot is provided with a first filter screen capable of preventing the water outlet 30111 of the flowerpot from being blocked by plant roots.

Preferably, the control system 2 includes a toppling switch capable of automatically cutting off the power when the air purifier is toppling, ensuring safety of use.

Preferably, the flowerpot assembly 301 further includes a flowerpot support 3012 configured to support the flowerpot 3011, a flowerpot sealing ring 3013 configured to seal the flowerpot 3011 and the flowerpot support 3012, and a flowerpot cover 3014 configured to close the flowerpot 3011. Two flowerpot supports 3012 can be provided, corresponding to the front and the rear of the flowerpot respectively, to secure the firmness. By providing the flowerpot sealing ring 3013, it is capable of preventing the water from splashing out of the flowerpot 3011 during the movement. After removing the flowerpot cover 3014, it is capable of injecting water into the water tank 303 through the flowerpot 3011 directly. The structure thereof is simple and compact and it is easy to operate.

Preferably, the microorganism box 302 is detachably connected with the shell 1 or the water tank 303, to facilitate the removal of the microorganism box 302 and water injection into the water tank and to clean the water tank. The structure thereof is simple and compact and it is easy to operate.

Preferably the water tank 303 is provided with a water level sensor connected with the control system 2. The water level sensor may be connected with the display 203 or the water tank is provided with a viewing window and a water level scale to facilitate the viewing of the water volume in the water tank.

Preferably, the air purifier is further provided with a water adding inlet capable of adding water from outside, the water adding inlet being provided with a second filter screen; the water adding inlet is in direct communication with the water tank 303 through a water pipe assembly, or the water adding inlet is provided on the flowerpot 3011, so that the water adding inlet is in fluid communication with the water tank 303 by the communication between the water adding inlet and the flowerpot 3011, to facilitate adding water from outside into the air purifier. When the water level sensor is provided in the water tank and the water adding inlet is connected to the tap, the air purifier is controlled to add water automatically with the controller, which is easier to use.

Preferably, the flowerpot 3011 is of cone shape; the flowerpot 3011 is positioned above the air outlet 102, and purified air exhausted from the air outlet 102 is blown upwards to the bottom and/or the outer surface of the flowerpot 3011, leaving the purified air blocked to change the wind direction to form a turbulent flow. It is beneficial to accelerate the air flow, and in particular when used indoors, it can improve the air purification efficiency greatly.

Preferably, an air outlet cover is provided on the air outlet 102; the air outlet cover is provided with a plurality of vents distributed in dots, and the purified air exhausted from the vents is blown to the bottom and/or the outer surface of the flowerpot 3011. Due to the different positions of the vents, the wind directions when being blocked are different as well. The airflows in all directions thus form a turbulent flow to accelerate the indoor air flow, which improves the air purification efficiency.

In order to facilitate the movement, a caster wheel can be provided on the bottom of the air purifier.

When in use, the microorganism fillers are replenished into the microorganism box, and hydroponics plants are planted on the flowerpot assembly, wherein the plant roots extend under the water to form a symbiosis relationship with the microorganisms in water. When the fan is enabled, the air flow is accelerated. The large particle dusts in the air are blocked out of the purifier by the primary filtering layer and the secondary filtering layer, and the fine particle dusts and VOCs are adsorbed on the water curtain. When the water circulation is started, the water is supplied to the water curtain with the water diverter assembly. When the water flows through the water curtain, the microorganisms in the water purify a part of the dusts and VOCs adsorbed on the water curtain, and the water brings the other part of the dusts and VOCs into the microorganism box. The VOCs are purified in the microorganism box, and the dusts are purified in the flowerpot. When the water filters through the microorganism box, it brings a part of the microorganisms into the water tank. The microorganisms enter into the flowerpot to have a symbiosis with the plant roots in water. The microorganisms purify the dusts and VOCs as they circulate along the water circulation between the water curtain, the microorganism box, the flowerpot and the water tank.

The purifier has a simple and compact structure, and the operations of the air purifying process are simple. It is capable of removing the indoor dusts and VOCs and other toxic and harmful gases effectively, and capable of replenishing the indoor humidity and improving the living environmental comfort. The purifier uses efficient microorganisms to deal with the toxic and harmful gases, which is environment friendly, scientific and efficient. The employed microorganisms are harmless to human body. Meantime, there are also provided a water circulation and ultraviolet lamp assembly to prevent the forming of microbial aerosols and the escaping of microorganisms. The filtering materials used in the purifier may be washed directly, thus don't need to be replaced, thus it is low in maintenances.

What is claimed is:

1. An air purifier, comprising:
   a shell provided with an air inlet and an air outlet; and further including:
   a control system, and an ecological purification system and a filtering system which are connected to the control system; water in the ecological purification system flowing through the filtering system, to bring dusts and VOCs adsorbed by the filtering system into the ecological purification system for purification, wherein the ecological purification system includes a flowerpot assembly configured for planting plants, a microorganism box configured for accommodating microorganisms and a water tank configured for holding water, arranged in sequence; wherein the flowerpot assembly includes a flowerpot provided with a water inlet and a water outlet; and the ecological purification system is provided with a following water circulation: water in the water tank enters the flowerpot via the water inlet of the flowerpot, and when a water level in the flowerpot is higher than the water outlet of the flowerpot, the water flows through the microorganism box via the water outlet of the flowerpot, and then enters the water tank.

2. The air purifier of claim 1, wherein the filtering system comprises a filtering layer including a primary filtering layer, a secondary filtering layer capable of adsorbing dusts and a water curtain capable of adsorbing VOCs and dusts, which are arranged in sequence between the air inlet and the air outlet; both ends of the water curtain being respectively in fluid communication with the water outlet of the flowerpot and the microorganism box.

3. The air purifier of claim 2, wherein the ecological purification system further comprises a water diverter assembly provided between the flowerpot and the water curtain, wherein the water diverter assembly is provided with at least one water outlet and at least one water inlet; the water inlet of the water diverter assembly is in fluid communication with the water outlet of the flowerpot, and the water outlet of the water diverter assembly is in fluid communication with the water curtain.

4. The air purifier of claim 3, wherein the microorganism box is provided therein with fillers which are capable of adsorbing dusts, VOCs and microorganisms; a drainage outlet is provided at the bottom of the water tank, the drainage outlet being detachably connected with a closing element matching therewith; the water curtain is formed by folding a water absorbent material and/or an antibacterial material; and the ecological purification system further includes a water pump connected to the control system, and a drawing pipe assembly connected with the water pump, and configured to introduce the water from the water tank to the water inlet of the flowerpot.

5. The air purifier of claim 1, wherein the flowerpot is further provided with an overflow hole positioned higher than the water outlet of the flowerpot; the ecological purification system further includes a return pipe assembly connected to the overflow hole of the flowerpot so as to introduce excessive water into the water tank when the water level in the flowerpot is higher than the overflow hole.

6. The air purifier of claim 1, wherein the air purifier further comprises a monitor connected to the control system and configured to monitor air quality.

7. The air purifier of claim 1, wherein the control system comprises a circuit board, a function key and a display.

8. The air purifier of claim 1, wherein the water outlet of the flowerpot is provided with a first filter screen configured for preventing the water outlet of the flowerpot from being blocked by plant roots.

9. The air purifier of claim 1, wherein the control system comprises a toppling switch configured for automatically cutting off the power when the air purifier is toppling.

10. The air purifier of claim 1, wherein the filtering system further comprises a fan device connected with the control system, and the fan device includes a wind rotor, an electric motor configured for driving the wind rotor and a wind guide tube guiding the wind caused by the rotating of the wind rotor to the air outlet.

11. The air purifier of claim 10, wherein the air purifier further comprises an ultraviolet lamp assembly provided between the wind rotor and the air outlet.

12. The air purifier of claim 1, wherein the flowerpot assembly further comprises a flowerpot support configured to support the flowerpot, a flowerpot sealing ring configured to seal the flowerpot and the flowerpot support, and a flowerpot cover configured to close the flowerpot; the water tank is provided with a water-tank separator configured to seal the water tank and further to prevent the water in the water tank from overflowing when the air purifier is toppling, and the water-tank separator is provided inside or on the top of the water tank, and hermetically connected with the water tank.

13. The air purifier of claim 1, wherein the air purifier is further provided with a water adding inlet configured for adding water from outside, the water adding inlet being provided with a second filter screen; the water adding inlet is in direct communication with the water tank through a water pipe assembly, or the water adding inlet is provided on the flowerpot, so that the water adding inlet is in fluid communication with the water tank by the communication between the water adding inlet and the flowerpot; and the water tank is provided with a water level sensor connected with the control system.

14. The air purifier of claim 1, wherein the flowerpot is of cone shape; the flowerpot is positioned above the air outlet, and purified air exhausted from the air outlet is blown upwards to the bottom and/or the outer surface of the flowerpot, leaving the purified air blocked to change the wind direction to form a turbulent flow.

15. The air purifier of claim 1, wherein an air outlet cover is provided on the air outlet; the air outlet cover is provided with a plurality of vents distributed in dots, and the purified air exhausted from the vents is blown to the bottom and/or the outer surface of the flowerpot.

* * * * *